(12) United States Patent
Long et al.

(10) Patent No.: US 11,978,212 B2
(45) Date of Patent: May 7, 2024

(54) SYSTEM AND METHODS FOR SEGMENTATION AND ASSEMBLY OF CARDIAC MRI IMAGES

(71) Applicant: Dyad Medical, Inc., Allston, MA (US)

(72) Inventors: John Long, Shrewsbury, MA (US); Ronny Shalev, Brookline, MA (US)

(73) Assignee: Dyad Medical, Inc., Allston, MA (US)

( * ) Notice: Subject to any disclaimer, the term of this patent is extended or adjusted under 35 U.S.C. 154(b) by 0 days.

(21) Appl. No.: 18/305,841

(22) Filed: Apr. 24, 2023

(65) Prior Publication Data

US 2024/0054653 A1 Feb. 15, 2024

Related U.S. Application Data

(63) Continuation of application No. 17/087,742, filed on Nov. 3, 2020, now Pat. No. 11,636,603.

(51) Int. Cl.
*G06T 7/11* (2017.01)
*A61B 5/055* (2006.01)
*G06T 3/40* (2006.01)
*G06T 3/4007* (2024.01)
*G06T 7/194* (2017.01)

(52) U.S. Cl.
CPC ............... *G06T 7/11* (2017.01); *A61B 5/055* (2013.01); *G06T 3/4007* (2013.01); *G06T 7/194* (2017.01); *G06T 2207/10092* (2013.01); *G06T 2207/20081* (2013.01); *G06T 2207/30048* (2013.01)

(58) Field of Classification Search
CPC ......... G06T 7/11; G06T 3/4007; G06T 7/194; G06T 2207/10092; G06T 2207/20081; G06T 2207/30048; A61B 5/055
See application file for complete search history.

(56) References Cited

U.S. PATENT DOCUMENTS

| | | | |
|---|---|---|---|
| 8,146,598 B2* | 4/2012 | Matlock | A61M 16/0427 128/200.26 |
| 8,186,350 B2* | 5/2012 | Matlock | A61M 16/0427 128/207.14 |
| 8,195,269 B2* | 6/2012 | Bogoni | A61B 5/085 600/407 |
| 9,591,988 B2* | 3/2017 | Kuhara | A61B 5/352 |
| 10,368,777 B2* | 8/2019 | Zhou | A61B 5/0044 |
| 2015/0023578 A1* | 1/2015 | Li | G06T 7/0012 382/131 |
| 2016/0140751 A1* | 5/2016 | Jafarkhani | A61B 8/466 382/131 |
| 2017/0109881 A1* | 4/2017 | Avendi | G06T 7/11 |
| 2017/0199654 A1* | 7/2017 | Wu | G06F 3/04845 |

(Continued)

Primary Examiner — Mia M Thomas
(74) Attorney, Agent, or Firm — Burns & Levinson LLP; Bruce D. Jobse

(57) ABSTRACT

A method and system for image segmentation systems and related methods of automatically segmenting cardiac MRI images using deep learning methods. One example method includes inputting MRI volume data from a MRI scanner, segmenting the MRI volume data with a whole volume segmentation analysis module, assembling the segmented MRI volume data into a 3D volume assembly with a 3D volume assembly module, determining the 3D volume assembly for anatomic plausibility with an anatomic plausibility analysis module, and outputting a final segmented 3D volume assembly.

10 Claims, 15 Drawing Sheets

(56) References Cited

U.S. PATENT DOCUMENTS

| | | | |
|---|---|---|---|
| 2019/0205606 A1* | 7/2019 | Zhou | G06F 18/285 |
| 2020/0074214 A1* | 3/2020 | Boespflug | G06V 10/267 |
| 2020/0383584 A1* | 12/2020 | Osman | A61B 5/0044 |
| 2021/0335041 A1* | 10/2021 | Haslam | G16H 50/50 |
| 2022/0092771 A1* | 3/2022 | Itu | G06T 7/0012 |
| 2022/0101034 A1* | 3/2022 | Ekin | G06T 7/11 |
| 2022/0138951 A1* | 5/2022 | Long | A61B 5/055 |
| | | | 382/131 |
| 2022/0222781 A1* | 7/2022 | Jacob | G06N 3/084 |
| 2022/0222825 A1* | 7/2022 | Yaacobi | G06T 7/11 |
| 2023/0005153 A1* | 1/2023 | Gupta | G06T 7/0012 |

* cited by examiner

SYSTEM AND METHODS FOR SEGMENTATION AND ASSEMBLY OF CARDIAC MRI IMAGES

TECHNICAL FIELD

The invention relates to image segmentation systems and related methods of automatically segmenting cardiac MRI images using deep learning methods.

BACKGROUND

Cardiovascular diseases (CVDs) are one of the most common forms of heart disease, which is the leading cause of death in developed countries. Major advances have been made in cardiovascular research and practice aiming to improve diagnosis and treatment of cardiac diseases as well as reducing the mortality of CVD. In light of the latter, Magnetic resonance imaging (MRI) is the preferred non-invasive imaging technique utilized for qualitative and quantitative assessment of cardiac metrics such as stroke volume, ejection fraction, and strain.

Segmentation of the cardiac MRI images is often required for the calculation of cardiac metrics. Cardiac MRI image segmentation partitions the image into a number of semantically (i.e., anatomically) meaningful regions, based on which quantitative measures can be extracted, such as the myocardial mass, wall thickness, left ventricle (LV) and right ventricle (RV) volume as well as ejection fraction (EF) etc. Typically, the anatomical structures of interest for cardiac image segmentation include the LV, RV, left atrium (LA), right atrium (RA), and coronary arteries. The quantitative measures extracted from the cardiac image segmentation are crucial in the calculation of the cardiac metrics.

Currently, clinicians have been relying on manual approaches for cardiac MRI segmentation. It typically takes a trained expert approximately 20 minutes to analyze images of a single subject at two time points of the cardiac cycle, end-diastole (ED) and end-systole (ES). This is time consuming, tedious, and prone to subjective errors. To overcome the limitations of the manual approaches of cardiac MRI segmentation, convolutional neural networks have been used to achieve state of the art performance on many segmentation tasks of cardiac MRI image segmentation. However, the predicted segmentations from present models based on convolutional neural networks may lead to cardiac shapes that are anatomically improbable and positions that are medically implausible. The results from these present models are still unfit for day-to-day clinical use. Therefore, there is need for a computerized and automated cardiac MRI segmentation solution that can address the above-addressed limitations by reducing time and labor costs and by increasing reliability and reproducibility of anatomically plausible cardiac MRI segmentation.

SUMMARY

In one embodiment, a method for segmentation and assembly of cardiac magnetic resonance imaging (MRI) images is provided. The method includes inputting MRI volume data from a MRI scanner, segmenting the MRI volume data with a whole volume segmentation analysis module, assembling the segmented MRI volume data into a 3D volume assembly with a 3D volume assembly module, determining the 3D volume assembly for anatomic plausibility with an anatomic plausibility analysis module, and outputting a final segmented 3D volume assembly.

In another embodiment, a system for segmenting and assembling cardiac magnetic resonance imaging (MRI) images is provided. The system includes a MRI scanner for acquiring MRI volume data from a patient, a computer for processing the MRI volume data with a method for segmentation and assembly of cardiac magnetic resonance imaging (MRI) images where the method further includes inputting MRI volume data from a MRI scanner, segmenting the MRI volume data with a whole volume segmentation analysis module, assembling the segmented MRI volume data into a 3D volume assembly with a 3D volume assembly module, determining the 3D volume assembly for anatomic plausibility with an anatomic plausibility analysis module, and outputting a final segmented 3D volume assembly, and a display screen to display the final segmented 3D volume assembly generated by the method.

DESCRIPTION OF THE DRAWINGS

The accompanying drawings, which are incorporated in and constitute a part of the specification, illustrate various example methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. Furthermore, elements may not be drawn to scale.

DETAILED DESCRIPTION

Figure 1A:
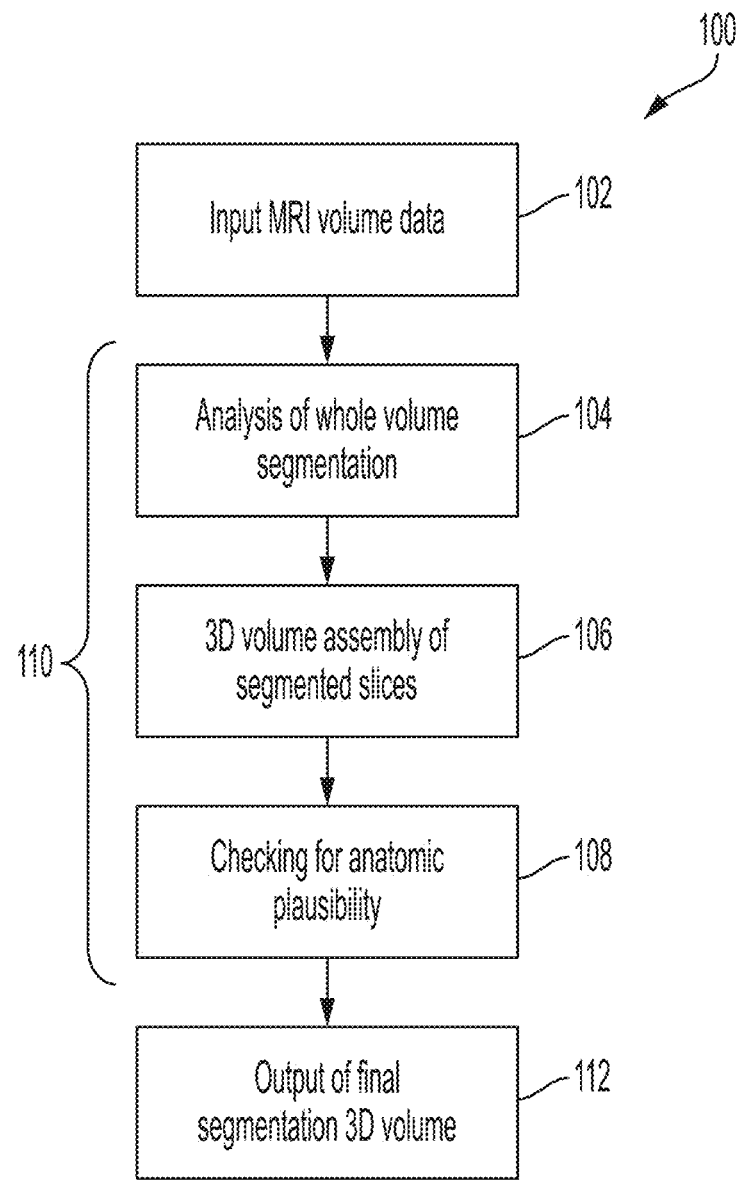
FIG. 1A illustrates a flowchart of an exemplary method for cardiac MRI segmentation in accordance with one illustrative embodiment.
Figure 1B:
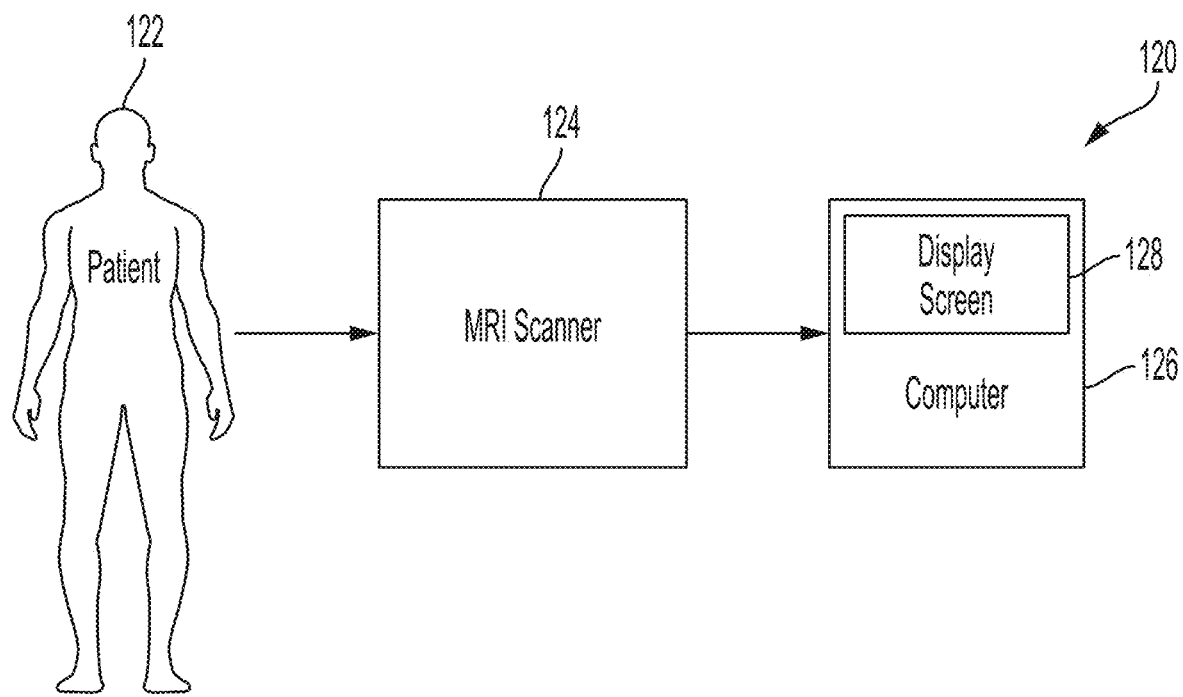
FIG. 1B illustrates a schematic of the exemplary method for cardiac MRI segmentation in accordance with FIG. 1A.

FIGS. 1A and 1B illustrate an exemplary method 100 and system 120 for cardiac MRI segmentation in accordance with one illustrative embodiment. The method 100 depicts the overview of an algorithm which accepts MRI volume data 102 as input and has a central processing segment 110 that includes a whole volume segmentation analysis module 104, 3D volume assembly module 106, and anatomic plausibility analysis module 108. The method 100 can be performed by a computer 126 connected to a MRI scanner 124 used to acquire images from a patient 122. The computer includes a display screen 128 to display the anatomically plausible segmented MRI images, as well as an assembled 3D volume of the segmented MRI images 112 which is computed by the method 100. The MRI volume data 102 comprises 2D slices of MRI heart volume 102 to the method 100 is a tensor of dimensions (256,256,1) and the assembled 3D volume of the segmented MRI images 112 is a tensor of dimensions (256,256,4). The input image of the MRI volume data 102 represents a single slice of the MRI scan at one point in time. The output, which is the assembled 3D volume of the segmented MRI images 112, is a one-hot labeling of each pixel in the input image. The size of the last dimension is 4 to represent the 4 classes of background, left ventricle, right ventricle, and myocardium.

In one embodiment, the automated algorithm of the computerized method 100 of FIG. 1A utilizes the input MRI volume data 102 from real clinical exams conducted with a MRI scanner 124 on patients 122. In the embodiment described above, the computerized method 100 was trained with MRI volume data 102 comprising short-axis MRI images from 4824 patients 122. The input MRI volume data 102 comprises MRI images consisting of an annotated volume for the end diastole and end systole stages. Annotated segments of the MRI images generally include a left ventricle, right ventricle, and myocardium.

Figure 2A:
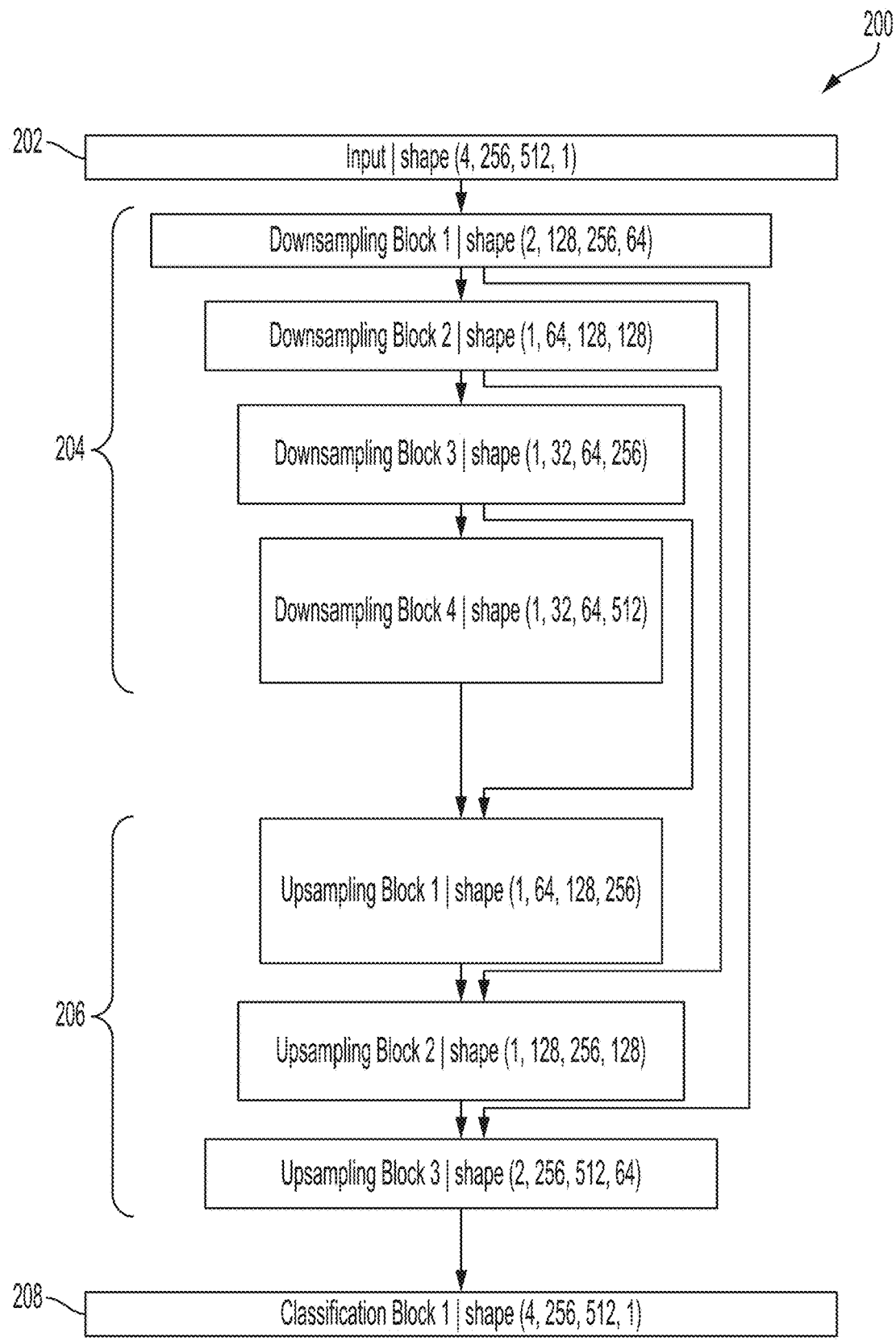
FIG. 2A illustrates a flowchart of an UNet convolutional network architecture of the exemplary method for cardiac MRI segmentation in accordance with FIG. 1A.
Figure 2B:
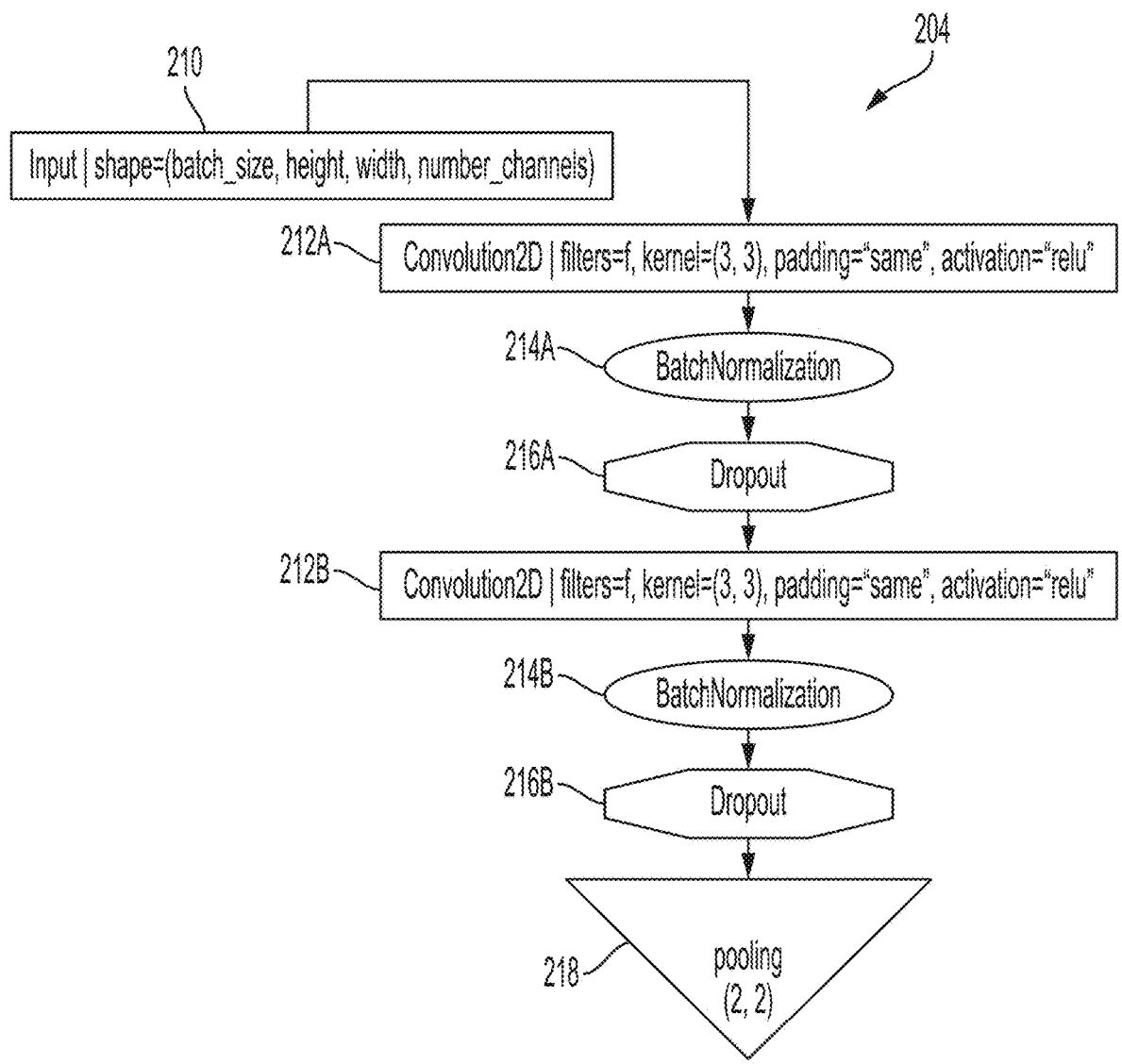
FIG. 2B illustrates a flowchart of an exemplary downsampling block of the UNet convolutional network architecture in accordance with FIG. 2A.
Figure 2C:
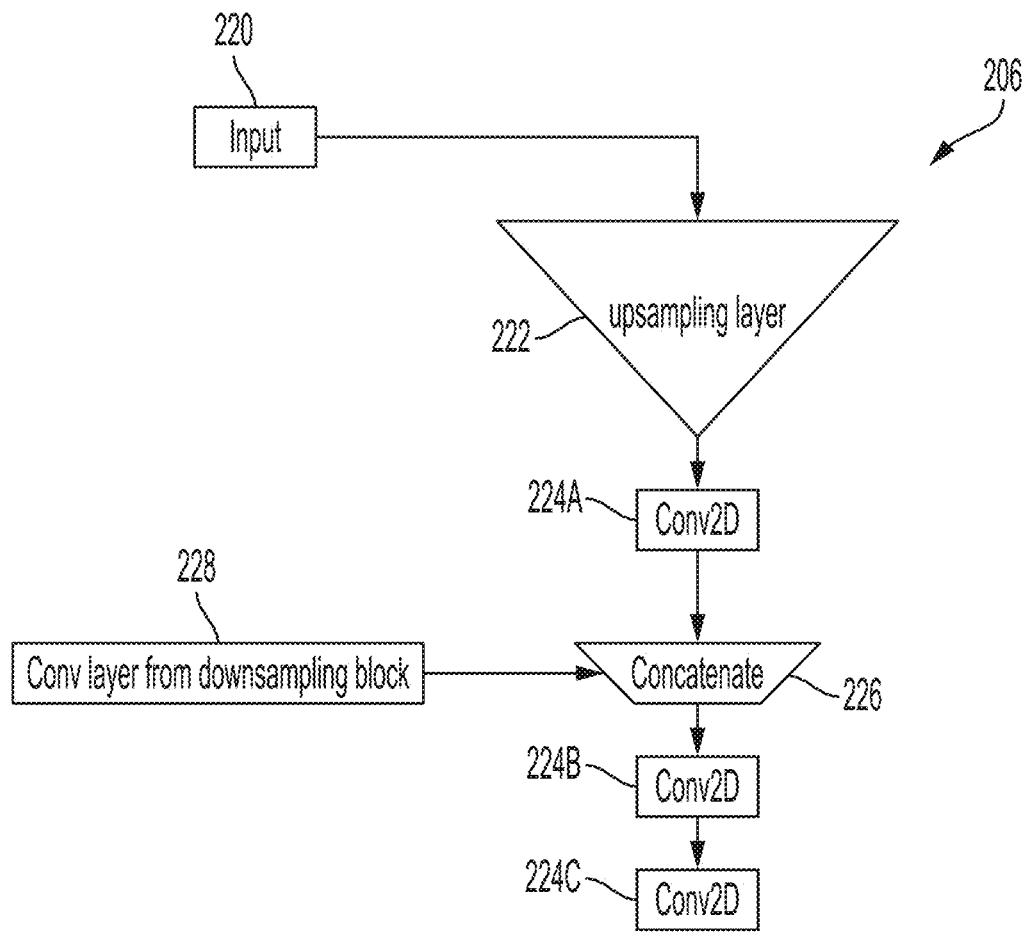
FIG. 2C illustrates a flowchart of an exemplary upsampling block of the UNet convolutional network architecture in accordance with FIG. 2A.

FIGS. 2A-2C illustrates a flowchart 200 of an illustrative UNet convolutional network architecture, an example downsampling block 204, and an example upsampling block 206 of the example method 100 for cardiac MRI segmentation in accordance with FIG. 1A. In the above-referenced embodiment, FIG. 2A presents an exemplary flowchart of the UNet convolutional network architecture 200 of the central processing segment 110. The UNet convolutional network architecture 200 includes an input 202, convolutional down sampling layers 204, expanding up sampling layers 206 and a classification block 208. In the up-sampling layers 206, feature maps from early layers of the same size are concatenated.

FIG. 2B illustrates a flowchart of the exemplary downsampling block 204 of the UNet convolutional network architecture 200 as presented in FIG. 2A. In this exemplary embodiment, the down sampling block 204 includes an input 210 and is parametrized with one nb_filters parameter that specifies the number of filters used in the convolution layers 212 and last layer of the block. The ordering of the layers in the downsampling block 204 is a convolutional layer 212A with activation function applied followed by batch normalization 214A and dropout 216A. This is followed by another convolutional layer 212B (with activation function), batch normalization 214B, dropout 216B and an output data pool 218. The purpose of the downsampling block 204 is to expand feature maps and gradually position each feature to where it lies in an original image of the input 210.

FIG. 2C illustrates a flowchart of an exemplary upsampling block 206 of the UNet convolutional network architecture 200 in accordance with FIG. 2A. In this exemplary embodiment, the upsampling block 206 includes an input 220 takes in two layers and a number specifying a number of filters as arguments. First the immediately preceding layer is up sampled through nearest neighbor interpolation to increase the size and put through a convolutional layer 224A. Then that layer is processed in a concatenating module 226 along with a convolution layer output 228 from the downsampling block 204 with the same image dimensions. This is followed by two additional convolution layers 224B, C. The final convolutional layer 208 comprises a 1×1 kernel and a number of filters equal to the number of classes. In this way, each pixel of the input image is classified into one of the classes in the classification block 208 succeeding the upsampling block 206.

Figure 3:
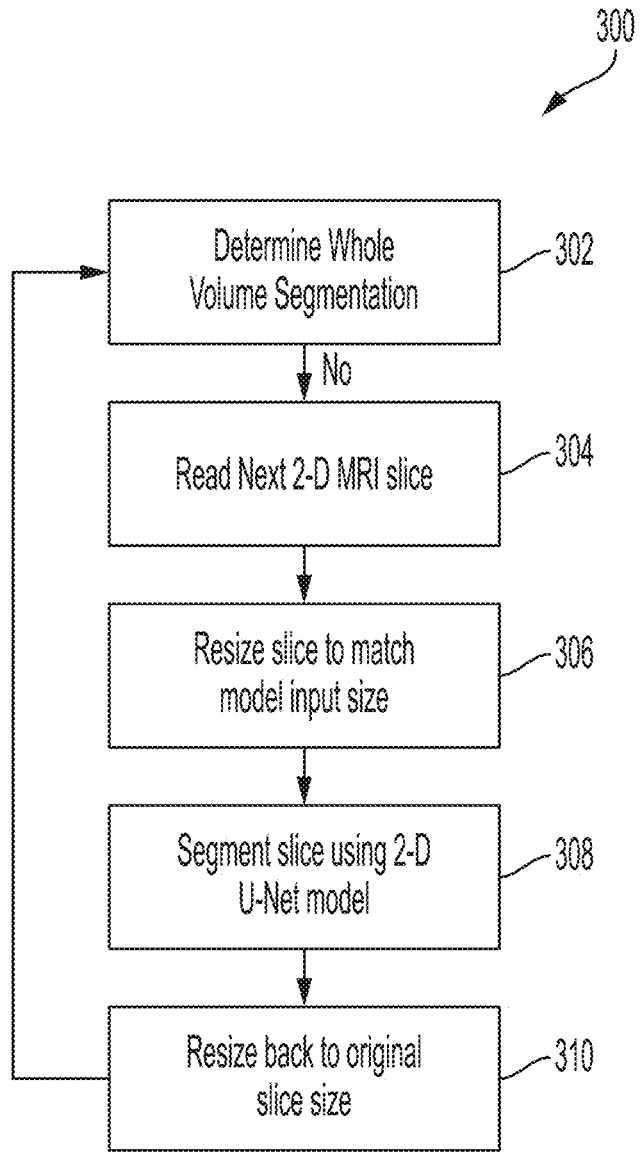
FIG. 3 illustrates a flowchart of an exemplary whole volume segmentation analysis module of the exemplary method for cardiac MRI segmentation in accordance with FIG. 1A.

FIG. 3 illustrates a flowchart 300 of the exemplary whole volume segmentation analysis module 104 of the example method 100 for cardiac MRI segmentation in accordance with FIG. 1A. The input MRI volume data 102 is analyzed by the whole volume segmentation analysis module 300 is assessed as a whole volume to first determine if there is whole volume segmentation 302. If it is determined that the input MRI volume data 102 is not segmented as a whole, the whole volume segmentation analysis module 300 proceeds to read the input MRI volume data 102 as a single 2D MRI slice at a time 304 following which the 2D MRI slice is subject to a resizing module 306. In the resizing module 306, the 2D MRI slices of the input MRI volume data 102 were resized with interpolation to match the input dimensions of the whole volume segmentation analysis module 104. Alternatively, the 2D MRI slices of the input MRI volume data 102 than the input dimensions, then a crop of the 2D MRI slices of the input MRI volume data 102 is selected. If the 2D MRI slices of the input MRI volume data 102 is smaller than the input dimensions, then the remaining space is padded with zeroes such that the padded image matches the model dimensions.

In one embodiment, the input MRI volume data 102 is augmented by the resizing module 306 to increase the number of images used for training. One method used for augmenting the data is to adjust the scale of the input 2D MRI slices of the input MRI volume data 102. A random scale factor from 0.9 to 1.1 is chosen at which to resize the 2D MRI slice. Then on the rescaled 2D MRI slice, a random cropped selection would be chosen if the rescaled 2D MRI slice was larger than the input or zero padding applied if the rescaled 2D MRI slice was smaller. The input MRI volume data 102 is further augmented by randomly adding flips, rotations, and translations to the 2D MRI slices. The input MRI volume data 102 may also be further augmented by randomly adding noise. Every single 2D MRI slice is processed by the whole volume segmentation analysis module 104 until it is determined to have whole volume segmentation 302.

Figure 4:
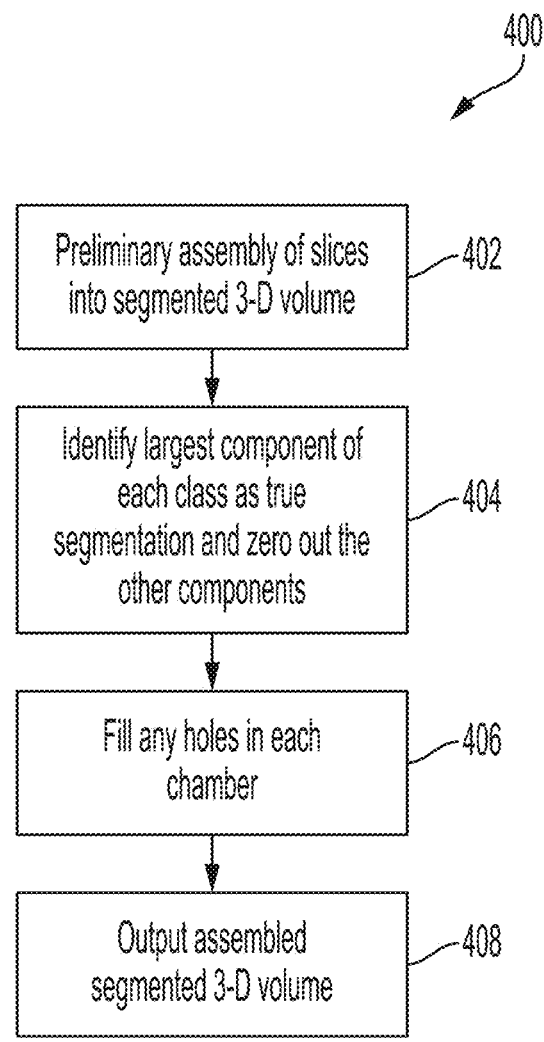
FIG. 4 illustrates a flowchart of an exemplary 3D volume assembly of segmented cardiac MRI images module of the exemplary method for cardiac MRI segmentation in accordance with FIG. 1A.

FIG. 4 illustrates a flowchart 400 of the exemplary 3D volume assembly of segmented cardiac MRI images module 106 of the example method 100 for cardiac MRI segmentation in accordance with FIG. 1A. Following the processing of the input MRI volume data 102 by the whole volume segmentation analysis module 104, the input MRI volume data 102 further processed via the 3D volume assembly of segmented cardiac MRI images module 106. The 2D MRI slices of the input MRI volume data 102 is assembled into a segmented 3D volume with a preliminary assembly module 402. Due to noise in the 2D MRI slices of the input MRI volume data 102, several cardiac chambers may be falsely detected by the 3D volume assembly module 106. A large component identification module 404 is then utilized to identify the largest/tallest component of each class as true segmentation and zero out other components. In one embodiment, the tallest/largest component, defined as the component spanning the most consecutive slices along the z-axis, is selected as the true component for each of the cardiac chambers. However, if there are multiple components with the same tallest height or multiple components with heights that differ by less than 3, then the component with the largest number of voxels is selected from the group of components with the largest heights. A chamber inspection module 406 is used to fill any holes in any of the assembled volumes of the heart chambers. A hole is defined as a small connected component of one class, such as a connected component for left ventricle, which is wholly surrounded by pixels of another class, such as myocardium. In this case, the pixels for left ventricle would be replaced with that for myocardium, thus filling the hole in the myocardium. Following this an assembled segmented 3D volume is created as an output 408.

Figure 5:
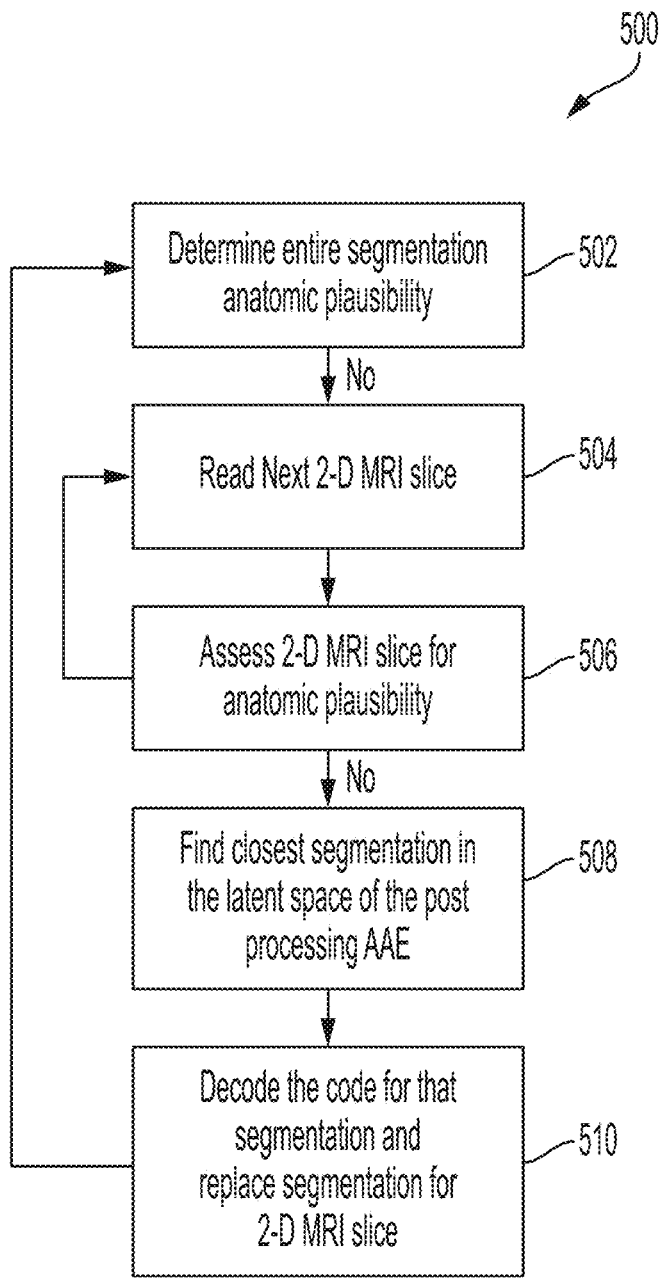
FIG. 5 illustrates a flowchart of an exemplary anatomical plausibility analysis module of the exemplary method for cardiac MRI segmentation in accordance with FIG. 1A.

FIG. 5 illustrates a flowchart 500 of the exemplary anatomical plausibility analysis module 108 of the example method 100 for cardiac MRI segmentation in accordance with FIG. 1A. Further to the 3D volume assembly of segmented cardiac MRI images module 106, the output 408 is analyzed for anatomic plausibility with the anatomical plausibility analysis module 108. The output 408 is analyzed for entire segmentation anatomic plausibility with a preliminary anatomic plausibility module 502. Following the processing with the preliminary anatomic plausibility module 502, the output 408 is read one 2D MRI slice 504 at a time and assessed for anatomic plausibility 506 for each slice. The 2D MRI slice that was determined to not be anatomically plausible are subject to a slice segmentation module 508 and the code for the 2D MRI slice segmentation is decoded and replaced with the anatomically plausible segmentation for the 2D MRI slice 510. This process is repeated for every 2D MRI slice with the anatomical plausibility analysis module 108 until the segmented cardiac 3D volume is entirely anatomically plausible.

Figure 6A:
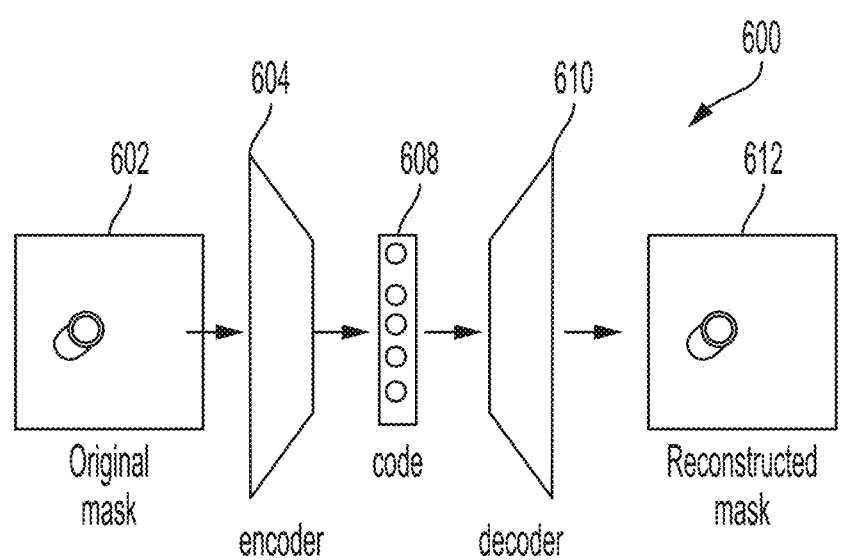
FIG. 6A illustrates a schematic of an exemplary mask autoencoder used in the training of the exemplary method for cardiac MRI segmentation in accordance with FIG. 1A.
Figure 6B:
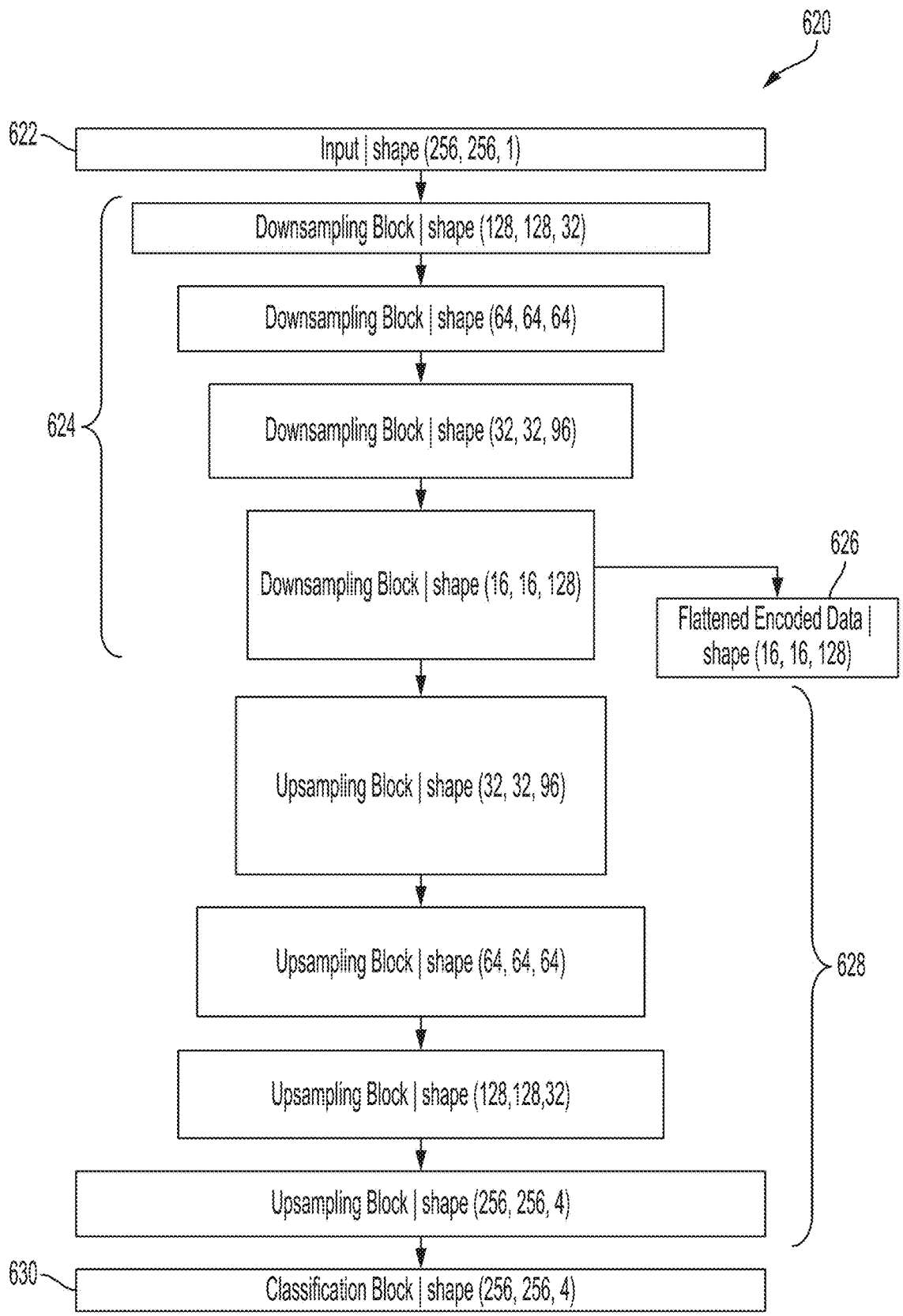
FIG. 6B illustrates a flowchart of a modified UNet convolutional network architecture of the exemplary mask autoencoder in accordance with FIG. 6A.
Figure 6C:
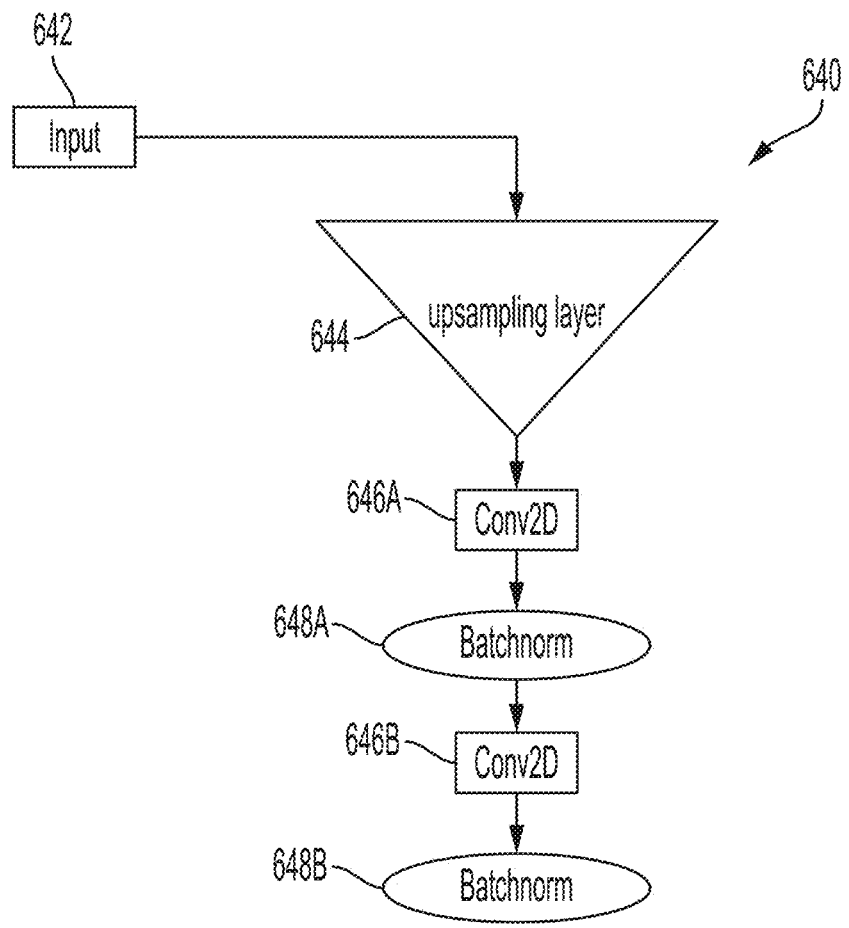
FIG. 6C illustrates a flowchart of an exemplary upsampling block of the UNet convolutional network architecture of the modified UNet convolutional network architecture of the exemplary anatomical plausibility analysis module in accordance with FIG. 6B.

FIGS. 6A-6C illustrate a schematic of an exemplary mask autoencoder 600, a flowchart of a modified UNet convolutional network architecture 620, a flowchart of an exemplary upsampling block 630 of the UNet convolutional network architecture of the modified UNet convolutional network architecture used in the training of the exemplary method 100 for cardiac MRI segmentation in accordance with FIG. 1A. As shown in FIG. 6A, the mask autoencoder 600 is trained to encode segmentation masks into a lower-dimensional space to aid in constraining segmentation masks to be anatomically plausible. In the exemplary embodiment, an input original mask 602 to the mask autoencoder 600 is a multi-channel one-hot encoded label mask that is processed by an encoder 604, code 608, and a decoder 610 to produce an output reconstructed mask 612 with channels equal to the number of label classes.

FIG. 6B illustrates a flowchart of a modified UNet convolutional network architecture 620 of the exemplary mask autoencoder 600 in accordance with FIG. 6A. The modified UNet convolutional network architecture 620 of the exemplary anatomical plausibility analysis module 108 includes an input 622, convolutional down sampling layers 624, expanding up sampling layers 628 and a classification block 630. Additionally, as part of the mask autoencoder 600, the modified UNet convolutional network architecture 620 also includes a flattening layer 626 that lead to a flattened code, which can be used to produce the output reconstructed mask 612 with channels equal to the number of label classes. Additionally, modified UNet convolutional network architecture 620 also includes a modified upsampling block 640 as presented in FIG. 6C. In this exemplary embodiment, the modified upsampling block 640 includes an input 642 with a upsampling layer 644, followed by two convolution layers 646 A,B with each have succeeding batch normalization modules 648 A,B. The modified upsampling block 640 further differ in that there are no longer skip connections from earlier blocks into later blocks. This lack of skip connections is due to requirement of the decoder 610 the mask autoencoder 600 to decode from the flattening layer 626 alone without using any of the previous layers before the flattening layer 626.

Figure 7:
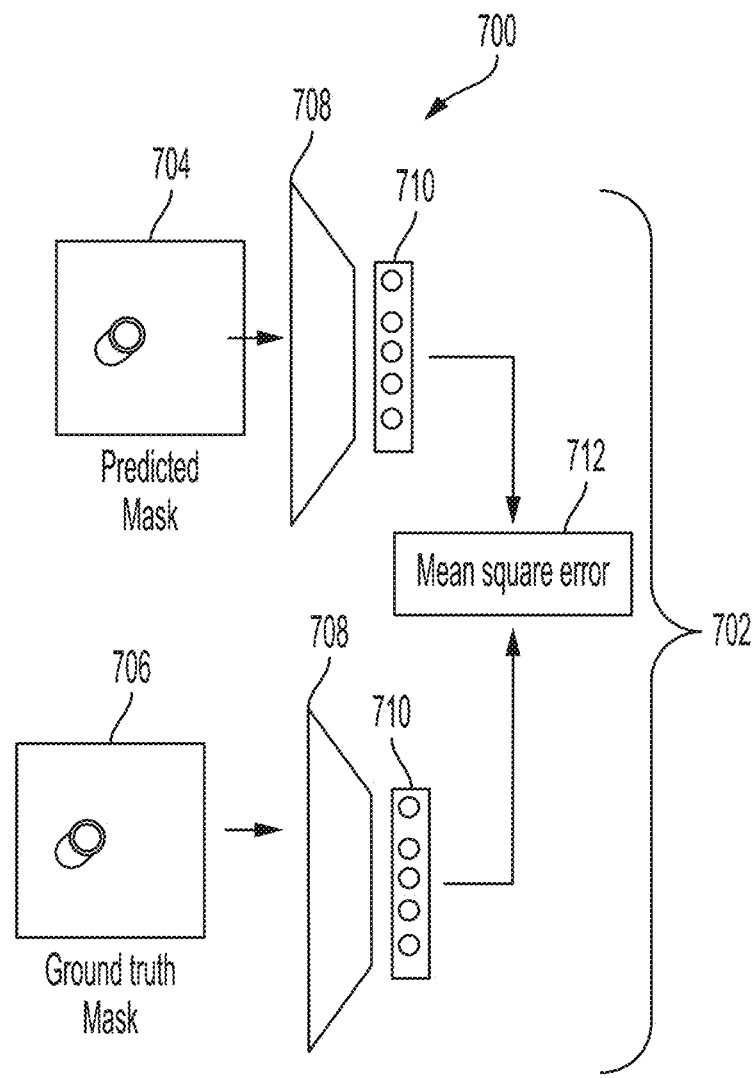
FIG. 7 illustrates a schematic of an exemplary mask autoencoder loss training scheme of the exemplary mask autoencoder in accordance with FIG. 6A.

FIG. 7 illustrates a schematic of an exemplary mask autoencoder loss training scheme 700 of the exemplary mask autoencoder 600 in accordance with FIG. 6A. The exemplary mask autoencoder 600 is trained with a cross-entropy loss function. The cross-entropy loss function is weighted such that rarer class examples contribute more to the loss than examples from common classes. In one embodiment, the cross-entropy loss function used is:

Heart Segmentation Minibatch Loss =

$$\sum_{i-pixels\ in\ minibatch} \left( w_{background} * y^{(i)}_{background} * \log\left(model\_pred(x^{(i)})_{background}\right) + \right.$$

$$w_{leftventricle} * y^{(i)}_{leftventricle} * \log\left(model\_pred(x^{(i)})_{leftventricle}\right) +$$

$$w_{rightventricle} * y^{(i)}_{rightventricle} * \log\left(model\_pred(x^{(i)})_{rightventricle}\right) +$$

$$\left. w_{myocardium} * y^{(i)}_{myocardium} * \log\left(model\_pred(x^{(i)})_{myocardium}\right) \right)$$

where the weights are respectively 0.01,0.4,0.4,0.19 for background, right ventricle, myocardium, and left ventricle and $(y^{(i)}_{background}, y^{(i)}_{left\ ventricle}, y^{(i)}_{myocardium}, y^{(i)}_{right\ ventricle})$ is a one-hot encoded vector for the class label of the i-th pixel. ADAM optimizer with a learning rate of 0.0001 was used to optimize the model over 500 epochs. Training was done over 500 epochs.

In another embodiment presented in the disclosure presented in FIG. 7, the mask autoencoder loss training scheme 700 is used to prevent anatomically implausible segments of predicted masks 704 by utilizing an autoencoder system 702 utilizing encoders 708 pre-trained on a ground-truth mask 706 and incorporating an autoencoder loss incorporated in codes 710 during training. The autoencoder loss code 710 used is:

AutoencoderLoss=MSE(encoded(segmentation),encode d(groundtruth))

The autoencoder system 702 has been pre-trained to encode segmentation masks of MRI images in a low-dimensional representation, so similar segmentations should have similar codes when encoded by the autoencoder system 702. Additionally, autoencoder codes 710 contain fewer dimensions than the input MRI images, similar representations may be mapped to the same autoencoder code 710 by the encoder 708 to calculate a mean square error 712 based on which noise should be removed. In the regularized training scheme, the segmentation model is trained using a loss function defined by:

Loss=A*SegmentationLoss+B*AutoencoderLoss

As training progresses, the A parameter decreases from 1 to 0 and the B parameter increases from 0 to 1.

Figure 8A:
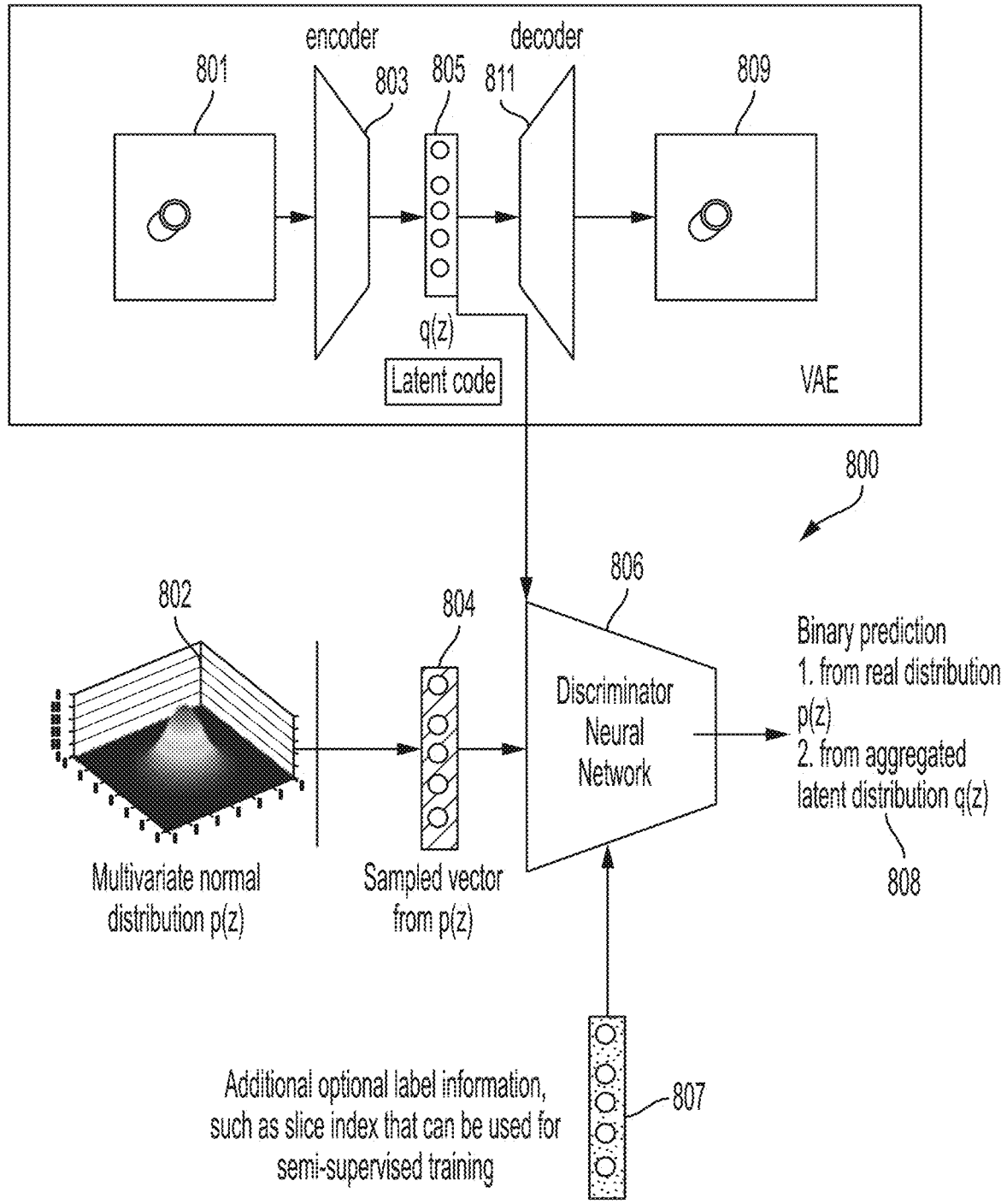
FIG. 8A illustrates a schematic of an exemplary adversarial variational autoencoder used in the training of the exemplary method for cardiac MRI segmentation in accordance with FIG. 1A.

In another embodiment, the anatomic plausibility module 108 is trained with a generative model, such as an adversarial variational autoencoder (aVAE) 800 as presented in FIG. 8A. The aVAE 800 is trained on cardiac segmentation masks to create a smooth manifold of latent codes that, when run through the autoencoder's decoder, have valid decodings to plausible cardiac segmentations. The aVAE 800 is trained in an adversarial manner, alternately training the aVAE 800 with an exemplary mask autoencoder 600 as presented in FIG. 6 and then training the encoder 803 and a discriminator 806 combined network in an adversarial manner. The discriminator 806 is a binary discriminator that is trained to distinguish true codes that come from the distribution p(z|x) of the VAE's encoder 803 and decoder 811 and false codes generated from a normal distribution 802 that is concatenated with label information. The discriminator 806 is a neural network that takes in a vector 801 with dimensions equal to the VAE latent code 805 and outputs 809 a binary label of either 0 or 1. The adversarial training is done by sampling a data set z from the distribution p(z|x) of the encoder 803 and then passing z through the discriminator 806. The combined encoder discriminator 806 is then trained through backpropagation with the output label as 1 for true 808. Then another sample z' 804 is drawn from the normal distribution 802 and adjoined with label information 807. Following this sample z' 804 is passed through the discriminator 806 and the discriminator is trained through backpropagation to predict 0 for false results 808.

Figure 8B:
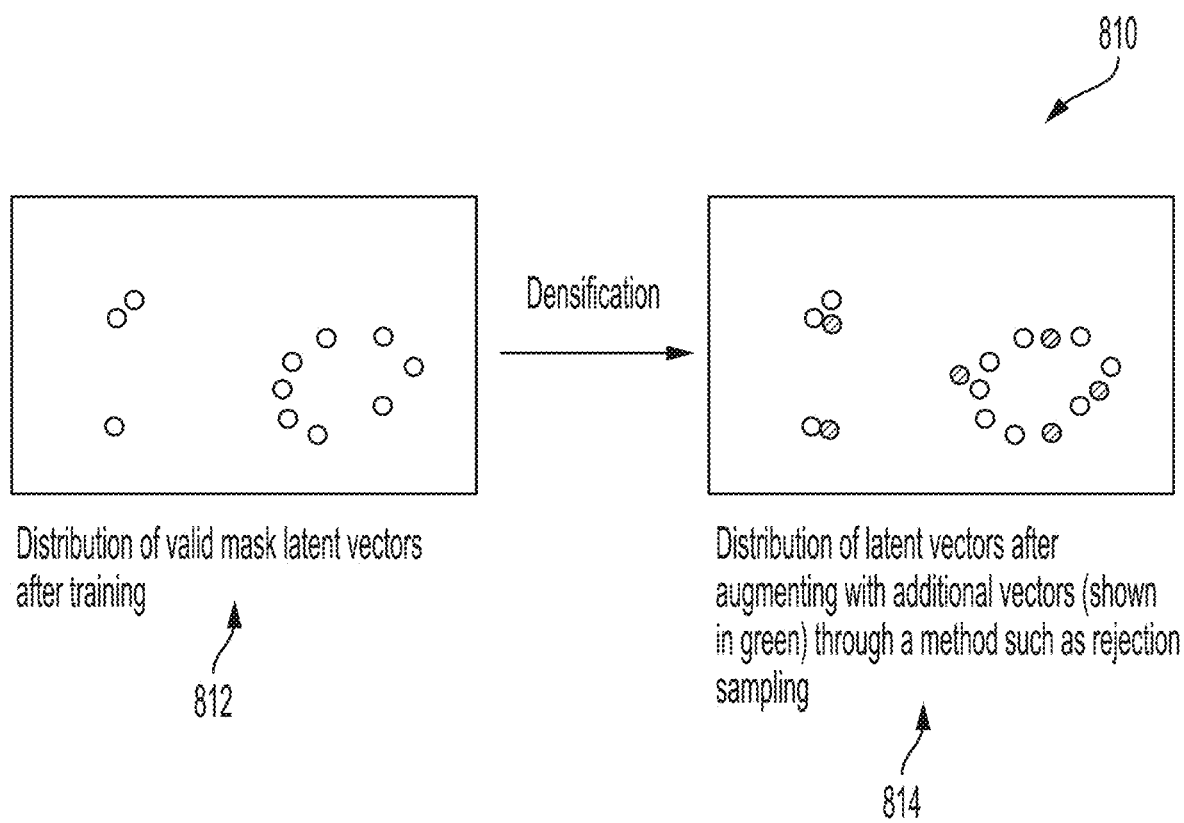
FIG. 8B illustrates a schematic of exemplary output masks of the distribution of latent mask vectors after initial training with the exemplary adversarial variational autoencoder in accordance with FIG. 8A.

FIG. 8B shows output masks 810 of the distribution of latent vectors in the latent space of the aVAE 800 after initial training of the aVAE 800 on approximately 20000 short-axis masks with and without augmentation with additional vectors. Output mask of training without augmentation 812 presents a good, well-populated latent space of latent codes for valid cardiac segmentations, providing one valid latent code for each short-axis mask used in training. Further methods of augmentation are employed to expand the number of valid latent codes and densely populate the latent space as depicted by the output mask with augmentation 814.

Figure 8C:
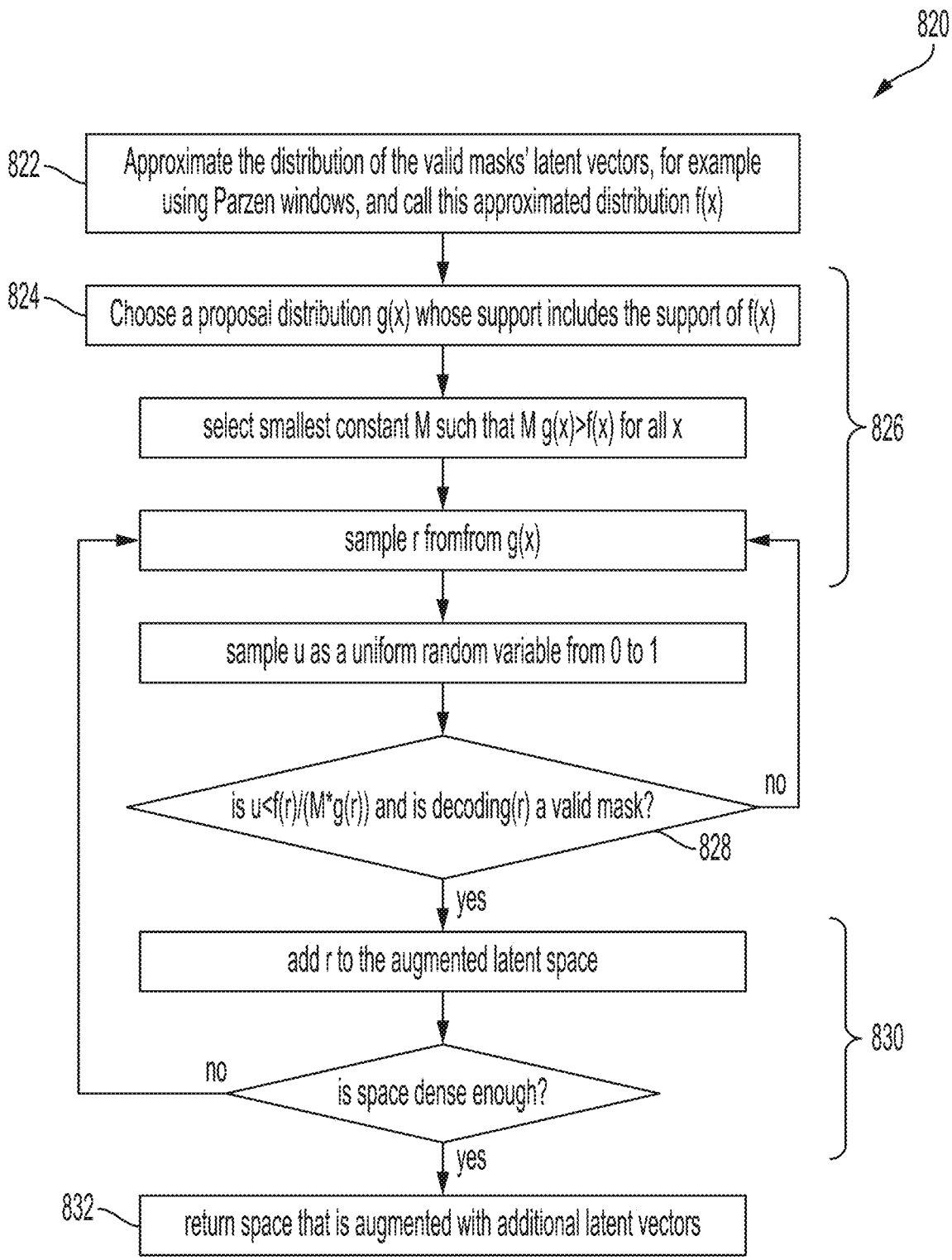
FIG. 8C presents an exemplary method of rejection sampling utilized for the exemplary output masks of the distribution of latent mask vectors in accordance with FIG. 8B.

FIG. 8C present a schematic of the rejection sampling method 820 utilized for augmentation and densification of the output mask 814 as presented in FIG. 8B. The method of rejection sampling 820 includes an approximation step 822 to generate a distribution of new latent codes that approximates a distribution P(z) of 20000 valid latent codes. In one embodiment, the approximation step 822 utilizes a Parzen windows approach to produce the approximated distribution. A proposal distribution 824 whose support includes the support of an approximated distribution, Q(z) is then chosen. In one embodiment, the rejection sampling method 820 utilizes custom crafted features 826 to determine the validity of a segmentation, such as whether the shape of a heart chamber exhibits an extreme concavity or whether the right ventricle and myocardium overlap. The rejection sampling method 820 uses a generative adversarial network (GAN) to compare the results of the custom crafted features 826 to generate masks and discriminate between generated and real masks and determine the validity of the decoded mask 828. The encoder 604 of the aVAE 800 further encodes the given segmentation into the latent space of the output masks 830. Then the closest latent code that decodes to a valid mask is found for the latent code of the given segmentation 832.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A method for segmentation and assembly of cardiac magnetic resonance imaging (MRI) images, the method comprising:
  acquiring MRI volume data;
  segmenting the MRI volume data with a whole volume segmentation analysis module;

assembling the segmented MRI volume data into a 3D volume assembly with a 3D volume assembly module;

determining the 3D volume assembly for anatomic plausibility with an anatomic plausibility analysis module; and outputting a final segmented 3D volume assembly, wherein the 3D volume assembly module further comprises a large component identification module to identify a largest connected component of each class as true segmentation and to zero out other components.

2. The method according to claim 1, wherein the whole volume segmentation analysis module further comprises a resizing module for resizing 2D MRI slices of the input MRI volume data with interpolation to match input dimensions of the input MRI volume data.

3. The method according to claim 1, wherein the 3D volume assembly module further comprising a chamber inspection module to fill holes of assembled 3D volume output of the large component identification module.

4. The method according to claim 1, wherein the method for segmentation and assembly of cardiac magnetic resonance imaging (MRI) images is trained with an adversarial variational autoencoder.

5. The method according to claim 4, wherein the adversarial variational autoencoder comprises a rejection sampling method for augmentation and densification of the 3D volume assembly.

6. A method for segmentation and assembly of cardiac magnetic resonance imaging (MRI) images, the method comprising:
    acquiring MRI volume data;
    segmenting the MRI volume data with a whole volume segmentation analysis module;
    assembling the segmented MRI volume data into a 3D volume assembly with a 3D volume assembly module;
    determining the 3D volume assembly for anatomic plausibility with an anatomic plausibility analysis module; and
    outputting a final segmented 3D volume assembly,
    wherein the anatomic plausibility analysis module further comprises a slice segmentation module for segmenting the 2D MRI slices of the input MRI volume data determined to not be anatomically plausible.

7. The method according to claim 6, wherein the slice segmentation module comprises:
    an encoder for encoding an input original mask;
    a code for processing of the encoded input original mask; and
    a decoder for outputting a reconstructed mask.

8. A method for segmentation and assembly of cardiac magnetic resonance imaging (MRI) images, the method comprising:
    acquiring MRI volume data;
    segmenting the MRI volume data with a whole volume segmentation analysis module;
    assembling the segmented MRI volume data into a 3D volume assembly with a 3D volume assembly module;
    determining the 3D volume assembly for anatomic plausibility with an anatomic plausibility analysis module; and
    outputting a final segmented 3D volume assembly,
    wherein the acquired MRI volume data is a tensor of dimensions (256, 256, 1).

9. A method for segmentation and assembly of cardiac magnetic resonance imaging (MRI) images, the method comprising:
    acquiring MRI volume data;
    segmenting the MRI volume data with a whole volume segmentation analysis module;
    assembling the segmented MRI volume data into a 3D volume assembly with a 3D volume assembly module;
    determining the 3D volume assembly for anatomic plausibility with an anatomic plausibility analysis module; and
    outputting a final segmented 3D volume assembly,
    wherein the final segmented 3D volume assembly is tensor of dimensions (256, 256, 4).

10. The method according to claim 9, wherein a last dimension of the final segmented 3D volume assembly represents classes of background, left ventricle, right ventricle, and myocardium.

* * * * *